United States Patent
Carnahan et al.

(10) Patent No.: US 6,565,810 B2
(45) Date of Patent: May 20, 2003

(54) METHOD AND APPARATUS FOR RAPID QUANTITATION OF A DIHYDRIC PHENOL

(75) Inventors: James Claude Carnahan, Niskayuna, NY (US); Ralph Joseph May, Niskayuna, NY (US)

(73) Assignee: General Electric Company, Niskayuna, NY (US)

(*) Notice: Subject to any disclaimer, the term of this patent is extended or adjusted under 35 U.S.C. 154(b) by 0 days.

(21) Appl. No.: 10/109,158

(22) Filed: Mar. 29, 2002

(65) Prior Publication Data

US 2002/0151079 A1 Oct. 17, 2002

Related U.S. Application Data

(62) Division of application No. 09/766,061, filed on Jan. 22, 2001.

(51) Int. Cl.[7] .............................................. G01N 33/48
(52) U.S. Cl. ...................... 422/68.1; 422/82.09; 436/131
(58) Field of Search .......................... 436/52, 131, 164, 436/53, 144; 568/700, 723, 706; 422/68.1, 82.09

(56) References Cited

U.S. PATENT DOCUMENTS

| | | |
|---|---|---|
| 1,977,627 A | 10/1934 | Greenhalgh |
| 2,359,242 A | 9/1944 | Perkins et al. |
| 2,623,908 A | 12/1952 | Stoesser et al. |
| 3,242,219 A | 3/1966 | Farnham et al. |
| 3,394,089 A | 7/1968 | McNutt et al. |
| 4,163,116 A | 7/1979 | Hedges et al. |
| 4,201,978 A | 5/1980 | Nally |
| 4,217,438 A | 8/1980 | Brunelle et al. |
| 5,602,755 A | 2/1997 | Ashe et al. |
| 5,684,580 A | 11/1997 | Cooper et al. |
| 5,712,481 A | 1/1998 | Welch et al. |
| 5,723,689 A | 3/1998 | Pressman et al. |
| 5,747,806 A | 5/1998 | Khalil et al. |
| 5,840,256 A | 11/1998 | Demers et al. |
| 5,846,396 A | 12/1998 | Zanzucchi et al. |
| 5,854,684 A | 12/1998 | Stabile et al. |
| 5,985,120 A | 11/1999 | Cholli et al. |
| 5,985,356 A | 11/1999 | Schultz et al. |
| 5,990,362 A | 11/1999 | Pressman et al. |
| 6,034,775 A | 3/2000 | McFarland et al. |
| 6,045,671 A | 4/2000 | Wu et al. |

FOREIGN PATENT DOCUMENTS

WO  009255  2/2000

OTHER PUBLICATIONS

Behrman, E. Analytical Chemistry (1964) vol. 36, pp. 2189–2191.*
"Encyclopedia of Chemical Processing and Design", vol. 4, pp. 407–430 (1977).
"PLS Regression Methods", by A. Huskuldsson, J. Chemometrics, vol. 2, pp. 211–228 91988).
"Partial Least–Squares Regression: A Tutorial", by P. Geladi et al., Anal. Chim. Acta., vol. 189, pp. 1–17 (1986).
"Number of Samples and Wavelengths Required for the Training Set in Near–Infrared Reflectance Spectroscopy", by D.E. Honigs et al., Appl. Spectosc., vol. 38, No. 6, pp. 844–847 (1984).

* cited by examiner

*Primary Examiner*—Jill Warden
*Assistant Examiner*—Sam P Siefke
(74) *Attorney, Agent, or Firm*—Noreen C. Johnson; Christian G. Cabou

(57) ABSTRACT

A method for determining the concentration of a dihydric phenol in the presence of a monohydric phenol uses spectroscopic detection at at least two wavelengths. Because the method does not require a chemical separation of the dihydric phenol and monohydric phenol, it is very rapid and particularly suitable for the analysis of large numbers of samples, such as those derived from combinatorial libraries.

4 Claims, 6 Drawing Sheets

METHOD AND APPARATUS FOR RAPID QUANTITATION OF A DIHYDRIC PHENOL

This application is a division of application Ser. No. 09/766,061, filed Jan. 22, 2001 which is hereby incorporated by reference in its entirety.

BACKGROUND OF THE INVENTION

The present invention relates to a method of determining the quantity of a dihydric phenol in an analytical sample. In particular, the invention relates to a rapid method for the quantitation of a dihydric phenol in the presence of a monohydric phenol.

Dihydric phenols are commercially important compounds used in the synthesis of polycarbonates, polyestercarbonates, polyesters, polyether sulfones, polyimides, and epoxies, among other polymers. Synthetic approaches to dihydric phenols include the catalyzed reaction of two equivalents of a monohydric phenol with one equivalent of a ketone to form the desired dihydric phenol and water; for example, the reaction of phenol with acetone to form 2,2-bis(4-hydroxyphenyl)propane (hereinafter "bisphenol A") is illustrated in the scheme below.

Scheme

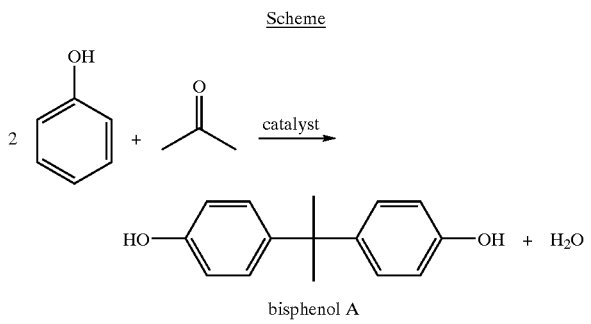

bisphenol A

Alternative syntheses include those substituting other carbon precursors, such as a geminal bis(acetoxy)alkane, for the ketone. These and other synthetic approaches are described, for example, in U.S. Pat. Nos. 1,977,627 to Greenhalgh, 2,359,242 to Perkins et al., 2,623,908 to Stoesser et al., 3,242,219 to Farnham et al., 3,394,089 to McNutt et al., 4,163,116 to Hedges et al., 4,201,878 to Mark et al., and 5,723,689 and 5,990,362 to Pressman et al.

All of the above described methods have in common the use of a monohydric phenol as a starting material to synthesize a dihydric phenol. This presents a challenge for quantitation of the dihydric phenol in the synthesis reaction mixture. Given their structural similarity, it is not surprising that monohydric and dihydric phenols have similar spectroscopic characteristics. For this reason, the progress of a dihydric phenol synthesis has typically been monitored by a liquid chromatographic method in which the dihydric phenol is separated from the monohydric phenol on an absorption column before quantitation by a method such as ultraviolet (UV) light absorption. Another method could be the use of gas chromatography or gas chromatography-mass spectrometry. Both of these methods require longer time per sample due to the separation phase and the time required to return the separation column to the initial conditions. While such methods enable the accurate quantitation of a dihydric phenol in the presence of a monohydric phenol, they usually require several minutes per sample.

Continuing efforts to discover new catalysts and reaction conditions for the synthesis of dihydric phenols may utilize combinatorial chemistry methods that generate many samples in a short period of time. Known methods for the quantitation of dihydric phenol in combinatorial samples are too slow to be practical for the analysis of the many samples constituting a combinatorial library of reaction conditions. There is therefore a need for a rapid method of quantifying a dihydric phenol in the presence of a monohydric phenol.

BRIEF SUMMARY OF THE INVENTION

The above-described and other drawbacks and disadvantages of the prior art are alleviated by an analytical method, comprising:

injecting into a flow analysis system a known volume of each of a plurality of analytical samples, each sample comprising a dihydric phenol and a monohydric phenol;

detecting the absorbance of the known volume of each analytical sample at at least two wavelength ranges; and determining the concentration of the dihydric phenol in each analytical sample based on the absorbance of the known volume of each analytical sample at at least two wavelength ranges;

wherein the method has a total analysis time not greater than about 5 minutes per sample.

DETAILED DESCRIPTION OF THE INVENTION

An analytical method comprises:

injecting into a flow analysis system a known volume of each of a plurality of analytical samples, each sample comprising a dihydric phenol and a monohydric phenol;

detecting the absorbance of the known volume of each analytical sample at at least two wavelength ranges; and determining the concentration of the dihydric phenol in each analytical sample based on the absorbance of the known volume of each analytical sample at at least two wavelength ranges;

wherein the method has a total analysis time not greater than about 5 minutes per sample.

Figure 1:
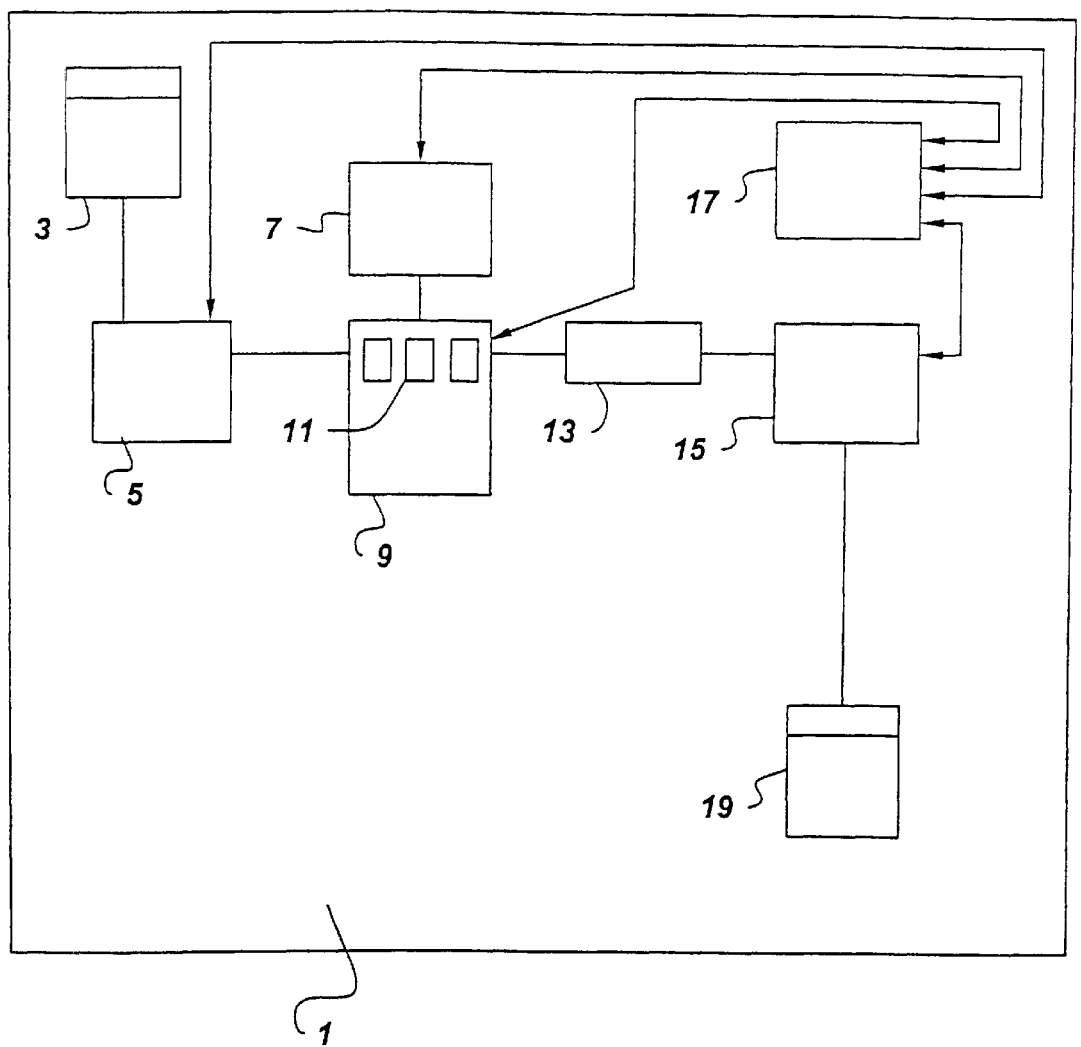
FIG. 1 is a schematic diagram of the analytical system.

As show in FIG. 1, the flow injection analytical system 1 may comprise a solvent delivery system 5; a sample injector 9 for injecting into the flow analysis system a known volume of each of a plurality of analytical samples, each analytical sample 11 comprising a dihydric phenol and a monohydric phenol; an absorbance detector 15 for detecting the absorbance of the known volume of each analytical sample at at least two wavelength ranges; and a computer 17 for determining the concentration of the dihydric phenol in each analytical sample based on the absorbance of the known volume of each analytical sample at at least two wavelength ranges. The analytical system 1 may additionally comprise a solvent reservoir 3 and a waste reservoir 19. The flow injection analysis system does not comprise a means for separating chemical components within the system flow, and it is therefore distinguished from liquid chromatography systems with that capability.

There is no particular limitation on the solvent delivery system and the sample injector used in the analytical system. Solvent delivery systems are widely used in flow injection analysis systems, as well as liquid chromatography systems, and are commercially available from manufacturers such as Hewlett Packard (now Agilent Technologies, Inc.; 2850 Centerville Rd., Wilmington, Del., 19808), Perkin Elmer Corp. (761 Main Ave, Norwalk, Conn., 06859), Shimadzu Scientific Instruments (7102 Riverwood Drive, Columbia, Md., 21046), Waters Corp. (34 Maple St. Milford, Mass., 01757), ISCO Inc. (4700 Superior St., Lincoln, Nev., 68504), Gilson Inc., (300 West Beltline Hwy, Middleton, Wis. 53562), Dionex Corp., (1228 Titan Way, Sunnyvale, Calif. 94086), and Cole-Parmer Instrument Co. (625 East Bunker court, Vernon Hills, Ill., 60061). A presently preferred solvent delivery system is the HP 1050 system from Hewlett Packard. Sample injectors, also known as autoinjectors, are also widely employed and commercially available from manufacturers such as Agilent Technologies, Inc. (2850 Centerville Rd., Wilmington, Del., 19808), Perkin Elmer Corp. (761 Main Ave, Norwalk, Conn., 06859), Shimadzu Scientific Instruments (7102 Riverwood Drive, Columbia, Md., 21046), Waters Corp. (34 Maple St. Milford, Mass., 01757), Gilson Inc., (300 West Beltline Hwy, Middleton, Wis. 53562), and Dionex Corp., (1228 Titan Way, Sunnyvale, Calif. 94086). A presently preferred sample injector is the HP 1050 sample injector from Hewlett Packard. The known volume injected by the sample injector for each analytical sample may be the same for each sample or may vary between samples. Injected volumes are typically about 1 to about 500 microliters, preferably about 5 to about 500 microliters. Because the time required to inject a known volume of an analytical sample can comprise a significant fraction of the total analysis time, it is expressly contemplated to employ at least two sample injectors in the analytical system.

The absorbance detector may be any absorbance detector capable of detecting the absorbance of the known volume of each analytical sample at at least two wavelength ranges. It is preferred that the wavelength ranges be substantially non-overlapping. In other words, it is preferred that at least 90% of the sensitivity within any given wavelength range be confined to wavelengths not included in any other wavelength range. Although the absorbance detector may comprise two or more single wavelength range detectors in series, it is preferred to use a single detector capable of simultaneously detecting at least two wavelength ranges. Absorbance detectors having multi-wavelength absorbance capability are commercially available from, for example, Agilent Technologies, Inc. (2850 Centerville Rd., Wilmington, Del., 19808), Perkin Elmer Corp. (761 Main Ave, Norwalk, Conn., 06859), Shimadzu Scientific Instruments (7102 Riverwood Drive, Columbia, Md., 21046), Waters Corp. (34 Maple St. Milford, Mass., 01757), Gilson Inc., (300 West Beltline Hwy, Middleton, Wis. 53562), and Dionex Corp. (1228 Titan Way, Sunnyvale, Calif. 94086).

In a preferred embodiment, the absorbance detector may detect the absorbance at at least about 5, more preferably at least about 10, yet more preferably at least about 20 wavelength ranges. Highly preferred absorbance detectors include diode array detectors and other multi-sensor detectors capable of simultaneously determining absorbance at many wavelength ranges. Such detectors typically measure the absorbance at closely spaced regular intervals, for example every 1 or 2 nanometers. Diode array detectors are well known in the art, and presently preferred detectors include the HP 1050 diode array detector from Hewlett Packard.

The analytical system comprises a computer 17 for determining the concentration of the dihydric phenol in each analytical sample based on the absorbance of the known volume of each analytical sample at at least two wavelength ranges. There is no particular limitation on the computer that may be used. Suitable computers include those commercially available as consumer personal computers (PCs) or technical workstations.

There is no particular limitation on computer software employed by the method. Suitable software is commercially available. Presently preferred software packages may be third-party products that use the Matlab computing environment (MathWorks, Inc., Natick, Mass.). These packages are the PLS_Toolbox (Eigenvector Technologies Inc., Manson, Wash.) and the Chemometrics Expert Toolbox (Perkin Elmer Inc., Norwalk, Conn.). These packages can be readily incorporated spreadsheets containing the spectral data.

In a preferred embodiment, the analytical system further comprises a sample preparation module 7 to automatically prepare analytical samples from a plurality of combinatorial samples. Such sample preparation modules are commercially available and include, for example, the Quadra 96 Model 230 robotic liquid handling system, which can simultaneously transfer multiple samples from reaction array plates and dilute with solvent to provide concentrations suitable for analysis. Other robotic devices that can transfer and dilute reaction products singly or in parallel include instruments from Gilson, Hamilton, Zinnser, Packard instruments, and others.

In another preferred embodiment, the analytical system comprises a mixer 13 for ensuring some concentration and time dispersion of the sample plug as it flows through the system. Suitable mixers include static mixers, tube coils, larger diameter sections in the flow system or inert bed columns. Mixers are well known in the art and commercially available from, for example, Alltech Associates Inc. (2051 Waukegan Rd., Deerfield, Ill., 60015) and The Lee Company (2 Petipaug Rd., Westbrook, Conn. 06498).

In a highly preferred embodiment, the analytical system is automated so that preparation and analysis of a plurality of analytical samples are prepared and analyzed without human intervention. Such automated methods may use a solvent preparation module for robotic preparation of solvent-containing analytical samples from a plurality of combinatorial samples, such as samples in a combinatorial library of dihydric phenol synthesis conditions. Methods and equipment, including commercially available equipment, for automating sample preparation and analysis are known to those of ordinary skill in the art. Solvent addition to polymers in array plates may be made in a single action via equipment such as Quadra 96 Model 230 automatic pipettors or serially by any of a number of commercially available dosing robots and pipettors. Manufacturers include, for example, Gilson, Hamilton, Zinnser, and Packard Instruments. Such automated methods for sample preparation and analysis may include the use of variable temperatures, pressures and atmospheres.

The method has an analysis time not greater than about 5 minutes per sample. It is preferred that the analysis time is not greater than 3 minutes per sample, more preferably not greater than 1 minute per sample, still more preferably not greater than about 30 seconds per sample, yet more preferably not greater than about 20 seconds per sample, even more preferably less than about 10 seconds per sample.

In the method, a plurality of analytical samples is analyzed. The exact number of analytical samples constituting a plurality may vary widely, from two to about one million or more. For example, the analytical samples may be derived from a combinatorial library comprising at least one 96-well plate. Much larger sample arrays are also known. For example, U.S. Pat. No. 5,854,684 to Stabile et al. describes analytical matrices comprising at least one million samples arranged in a density of at least about 10 sites per square centimeter, and U.S. Pat. No. 5,840,256 to Demers et al. provides details for a 7.25 square inch analytical matrix comprising 99,856 samples. Microscale reaction vessels and methods of delivering reagents to them are described in, for example, U.S. Pat. Nos. 5,846,396 to Zanzucchi et al., 5,985,356 to Schultz et al., and 6,045,671 to Wu et al.; and PCT International Application No. WO 2000/09255 to Turner et al.

Generally, each analytical site will comprise about 1 microgram to about 500 milligrams, preferably about 10 micrograms to about 50 milligrams, more preferably about 1 milligram to about 50 milligrams, for the total weight of the dihydric phenol and the monohydric phenol.

There is no particular limitation on the dihydric phenol except that it comprises at least one aromatic ring and at least two hydroxyl groups directly attached to the at least one aromatic ring.

Suitable dihydric phenols include those having the general formula

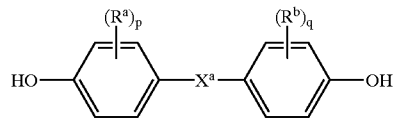

wherein $R^a$ and $R^b$ each independently represent a halogen atom or a monovalent hydrocarbon group having from 1 to about 12 carbon atoms; p and q are each independently integers from 0 to 4; and $X^a$ represents a group having the formula

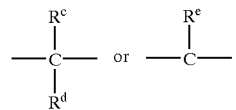

wherein $R^c$ and $R^d$ each independently represent a hydrogen atom or a monovalent linear or cyclic hydrocarbon group having from 1 to about 12 carbon atoms, and $R^c$ and $R^d$ may connect to form a cyclic hydrocarbon group; and $R^e$ is a divalent hydrocarbon group having from 1 to about 12 carbon atoms.

Some illustrative, non-limiting examples of dihydric phenols are disclosed by name or formula (generic or specific) in U.S. Pat. No. 4,217,438 to Brunelle et al. A nonexclusive list of specific examples of dihydric phenols includes the following: 1,1-bis(4-hydroxyphenyl)methane; 1,1-bis(4-hydroxyphenyl)ethane; 2,2-bis(4-hydroxyphenyl)propane (hereinafter "bisphenol A" or "BPA"); 2,2-bis(4-hydroxyphenyl)butane; 2,2-bis(4-hydroxyphenyl) octane; 1,1-bis(4-hydroxyphenyl)-propane; 1,1-bis(4-hydroxyphenyl)-n-butane; bis(4-hydroxyphenyl) phenylmethane; 2,2-bis(4-hydroxy-1-methylphenyl) propane; 1,1-bis(4-hydroxy-t-butylphenyl)-propane; bis(hydroxyaryl)alkanes such as 2,2-bis(4-hydroxy-3-bromophenyl)propane; 1,1-bis(4-hydroxyphenyl) cyclopentane; and bis(hydroxyaryl)cycloalkanes such as 1,1-bis(4-hydroxyphenyl)cyclohexane and 1,1-bis(3-methyl-4-hydroxyphenyl)cyclohexane; and the like, as well as combinations comprising at least one of the foregoing. In a preferred embodiment, the dihydric phenol comprises 2,2-bis(4-hydroxyphenyl)-propane.

The monohydric phenol present in the analytical sample may have the formula

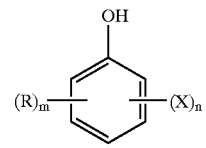

wherein R is $C_1$–$C_{12}$ alkyl; X is fluoro, chloro, bromo, or iodo; m is 0–4; and n is 0–4; with the proviso that $m+n \leq 4$. In a preferred embodiment, at least one ortho or para position is unsubstituted (i.e., at least one ortho or para position is substituted with hydrogen). In a highly preferred embodiment, the monohydric phenol comprises phenol (C.A.S. Registry No. 108-95-2).

The method is particularly useful when the spectroscopic quantification of the dihydric phenol is made difficult by the presence of a substantial amount of the monohydric phenol. Thus, in one embodiment, the molar ratio of the monohydric phenol to the dihydric phenol in at least one analytical sample is not less than about 1:1, and in another embodiment, the molar ratio of the monohydric phenol to the dihydric phenol in at least one analytical sample is not less than about 10:1. Dihydric phenol may be accurately quantified at even higher molar ratios of monohydric phenol to dihydric phenol, such as, for example, 500:1.

While the method comprises analysis of a plurality of samples, each comprising a dihydric phenol and a monohydric phenol, additional samples may be analyzed that do not comprise either a dihydric phenol or a monohydric phenol, or both. Such samples may be useful, for example to calibrate the method. For example, a blank sample may be used to determine the baseline absorbance. Also, samples containing either a monohydric phenol or a dihydric phenol but not both may be used to quantify the spectral characteristics of those respective analytes. Similarly, when the analytical samples are derived from individual sites on a combinatorial sample array, each site need not comprise both a dihydric phenol and a monohydric phenol as long as a plurality of site comprise both these materials. For example, the analytical samples may be prepared from a combinatorial sample array comprising a plurality of spatially differentiated sites, at least 50% of the sites comprising a dihydric phenol and a monohydric phenol.

In addition to the dihydric phenol and the dihydric phenol, one or more analytical samples may comprise a solvent. Suitable solvents are capable of dissolving the dihydric phenol and the monohydric phenol. Such solvents include, for example, acetonitrile; simple alcohols such as methanol, ethanol, isopropanol, and the like; ketones such as acetone, methyl ethyl ketone (MEK), and methyl isobutyl ketone (MIBK); ethers such as diethyl ether, tetrahydrofuran, dioxane, t-butylmethylether: and esters such as ethyl acetate. Preferred solvents include acetonitrile, methanol, ethanol, isopropanol, acetone, MEK, MIBK, with acetonitrile and methanol being highly preferred.

The concentration of the dihydric phenol in the solvent is not critical, but it should be sufficient to produce a peak signal with an intensity of at least 0.0005 absorbance units over the wavelength range of interest in a 10 mm path length cell.

In a preferred embodiment, each of the plurality of analytical samples comprises a dihydric phenol synthesis reaction mixture, which may comprise, in addition to at least one dihydric phenol and at least one monohydric phenol, an alkylene precursor, such as a ketone, including acetone; water; an intermediate in the synthesis of the dihydric phenol, such as, for example, 2-(4-hydroxyphenyl)-2-propanol; or a side product in the synthesis of the dihydric phenol, such as, for example, 2-(4-hydroxyphenyl)-2-(2-hydroxyphenyl)propane, 2,2-bis(2-hydroxyphenyl)propane, or Chroman-I

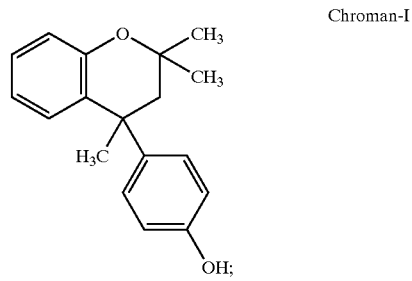

Chroman-I a catalyst or promoter, including mercaptans, thiophenols, thio acids, and ion exchange catalysts; and mixtures comprising at least one of the foregoing. These and various other reactants, solvents, catalysts, side-products and intermediates are described in references teaching procedures for the preparation of dihydric phenols, including, for example, U.S. Pat. Nos. 1,977,627 to Greenhalgh, 2,359,242 to Perkins et al., 2,623,908 to Stoesser et al., 3,242,219 to Farnham et al., 3,394,089 to McNutt et al., 4,163,116 to Hedges et al.; 4,201,878 to Mark et al.; and 5,990,362 to Pressman et al.; as well as "Encyclopedia of Chemical Processing and Design", volume 4, pages 407–430 (1977).

The method comprises determining the concentration of the dihydric phenol in each analytical sample based on the absorbance of the known volume of each analytical sample at at least two wavelength ranges. In view of the typical spectral characteristics of monohydric phenols and dihydric phenols, suitable wavelength ranges may comprise wavelengths of about 235 nm to about 350 mm, preferably about 250 nm to about 310 nm, more preferably about 260 nm to about 295 nm.

In a preferred embodiment, the at least two wavelength ranges comprise one wavelength of about 264 nm to about 272 nm and one wavelength of about 284 nm to about 292 nm.

In another preferred embodiment, the absorbance of the known volume of each analytical sample is detected at at least about 5 wavelength ranges, more preferable at at least about 10 wavelength ranges. Use of more than two wavelength ranges improves the precision with which the dihydric phenol is quantified.

The method comprises determining the concentration of the dihydric phenol in each analytical sample based on the absorbance of the known volume of each analytical sample at at least two wavelength ranges. Determining the concentration makes use of a correlation between sample concentration and a function comprising the sample absorbance at the at least two wavelength ranges. The function may be as simple as the ratio of the absorbance at two wavelength ranges. For example, as demonstrated in the working examples below, the ratio of absorbances at 288±1 and 268±1 nm ($A_{288}/A_{268}$) may be correlated with the concentration of bisphenol A in samples comprising bisphenol A and phenol.

In a preferred embodiment, correlation of the spectra to the species concentrations of interest is accomplished using multivariate analysis. The term "multivariate analysis" includes all types of multivariate statistical analysis, with the procedures known as partial least squares (PLS), principle components analysis (PCA), and multiple linear regression (MLR) being preferred. By the PCA method, each spectrum in the calibration sample set is represented as an n-dimensional vector, where n is the number of points in the spectrum. Each vector (spectrum), is broken down into one or more components, plus an error vector to account for variation not explained by the factors. By this mathematical treatment or "decomposition," the autoscaled spectrum is represented as the weighted vector sum of the components plus the error vector. Each successive component accounts for the variation remaining in the calibration set, after subtracting the weighted contributions of all preceding components. The coefficients in the weighted sums (also known as "scores") are then correlated with the properties of interest (e.g., species concentrations) using multilinear regression. PLS is similar to PCA in that the spectra are decomposed into components ("latent variables"). However, by the PLS method, the spectra are weighted by the species concentrations prior to the decomposition step. The regression is accomplished during the decomposition, making a separate regression step unnecessary. More detailed information on these methods can be found in the literature. See, for example, H. Martens and T. Naes, "Multivariate Calibration" (Wiley, N.Y., 1992); D. L. Massart, B. G. M. Vandeginste, L. M. C. Buydens, S. DeJong, P. J. Lewi and J. Smeyers-Verbeke, "Handbook of Chemometrics and Qualimetrics: Parts A & B" (Elsevier, Amsterdam, 1997); R. Kramer, "Chemometric Techniques for Quantitative Analysis" (Wiley, N.Y., 1998); P. Geladi and B. R. Kowalski, "Partial Least-Squares Regression: A Tutorial", *Anal. Chim. Acta,* volume 185, pages 1–17 (1986); A. Hoskuldsson, "PLS Regression Methods", *J. Chemometrics,* volume 2, pages 211–228 (1988); and D. E. Honigs, G. M. Hieftje, and T. Hirschfeld, "Number of Samples and Wavelengths Required for the Training Set in Near-Infrared Reflectance Spectroscopy", *Appl. Spectrosc.,* volume 38, number 6, pages 844–847 (1984).

The multivariate analysis techniques may preferably be applied to datasets including absorbances at at least 5, more preferably at least 10, yet more preferably at least 20 wavelength ranges. The precision of the method may also be improved by analyzing absorbance data corresponding to more than one elution time. In other words, the method may utilize absorbance data collected at multiple times as the sample passes through the absorbance detector. For example the method may utilize absorbance readings taken at least 2 times, at least 5 times, or at least 10 different times per sample for each wavelength range.

In a preferred embodiment, injecting a known volume of each analytical sample, detecting the absorbance of each analytical sample, determining the concentration of dihydric phenol in each analytical sample. and, optionally, preparing the analytical sample, may be conducted without human intervention.

In a highly preferred embodiment, the method comprises: injecting into a flow analysis system a known volume of each of a plurality of analytical samples comprising bisphenol A and phenol; mixing the known volume of each of a plurality of analytical samples using an in-line mixer; detecting the absorbance of the known volume of each analytical sample at at least ten wavelength ranges, each wavelength range comprising a wavelength of about 240 to about 310 nanometers; and determining a concentration of phenol and a concentration of bisphenol A in each analytical sample based on partial least squares analysis of the absorbance of the known volume of each analytical sample at at least ten wavelength ranges; wherein the total analysis time is not greater than about 10 seconds per sample.

The invention is further illustrated by the following non-limiting examples.

EXAMPLE 1

A Hewlett Packard model 1050 solvent delivery system and model 1050 sample injector, and a length of ⅛ inch outer diameter stainless steel tubing as a mixing zone were connected to a Hewlett Packard 1050 diode array detector and an HP Vectra XU 6/200 computer with a Windows 95 operating system and HP Chemstation software. The detector was set to collect spectra over the range of 220 to 400 nm with a resolution of 2 nm a sampling rate of 5 spectra per second. The flow rate of the acetonitrile solvent was 1.5 milliliters per minute (ml/min) giving an analysis time of about 3.0 minutes per sample. The injection volume was 25 microliters. Removal of the tubing length and substitution of a 50 microliter in-line static mixer (Alltech part No. 20141+20147 for core and shell) brings the analysis time to less than 1 minute per sample, where the cycle time of a single autosampler becomes rate limiting. Analysis cycle times as short as 15 seconds per sample can be achieved in this system by the addition of a second autosampler.

Figure 2:
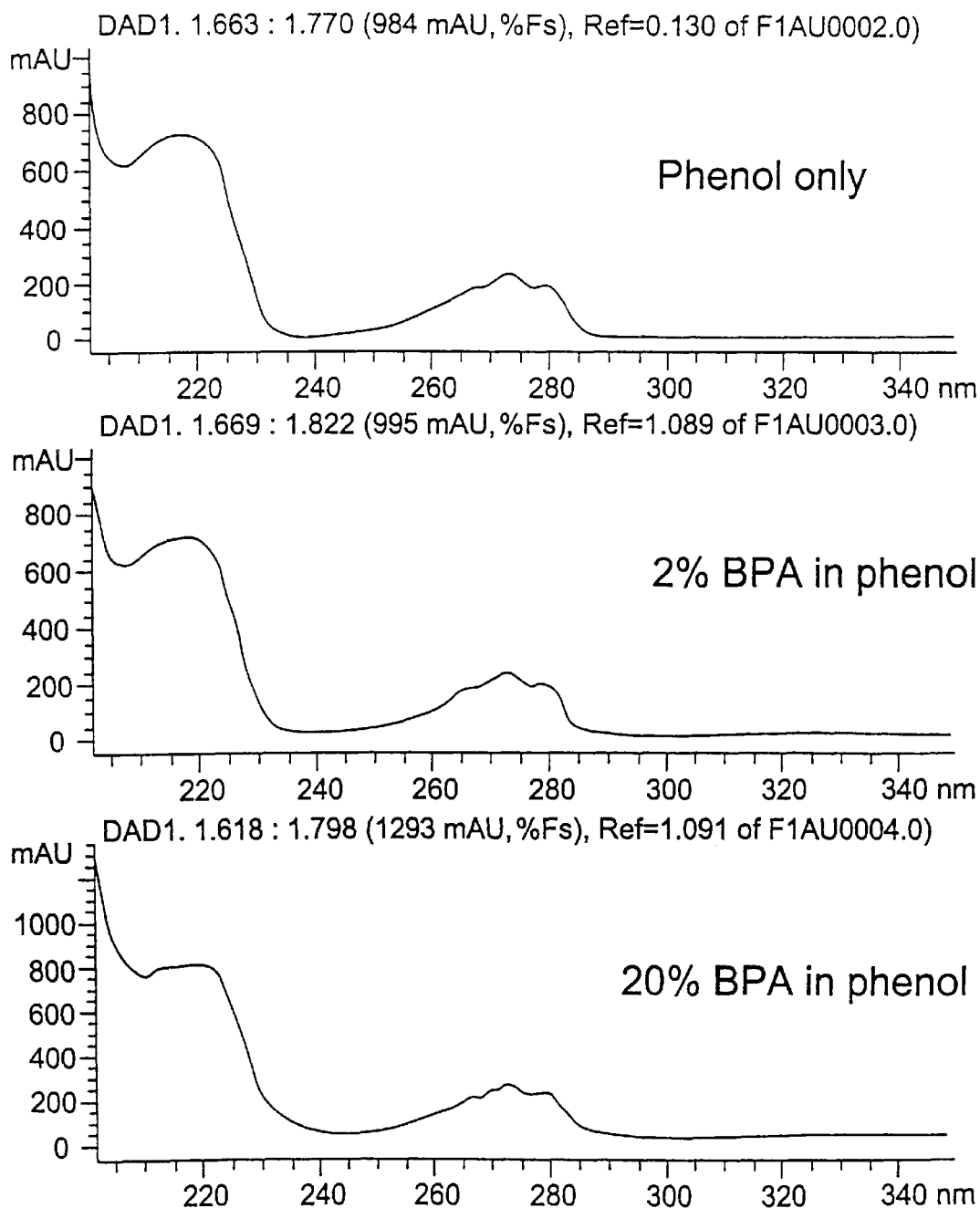
FIG. 2 shows plots of UV spectra at peak absorbance for 0, 2, and 20 weight percent bisphenol A in phenol dissolved in acetonitrile.

Overlay plots of the spectra corresponding to peak maxima for samples containing 0, 2, and 20 weight percent bisphenol A (BPA) and about 10 weight percent phenol dissolved in acetonitrile are shown in FIG. 2.

Figure 3:
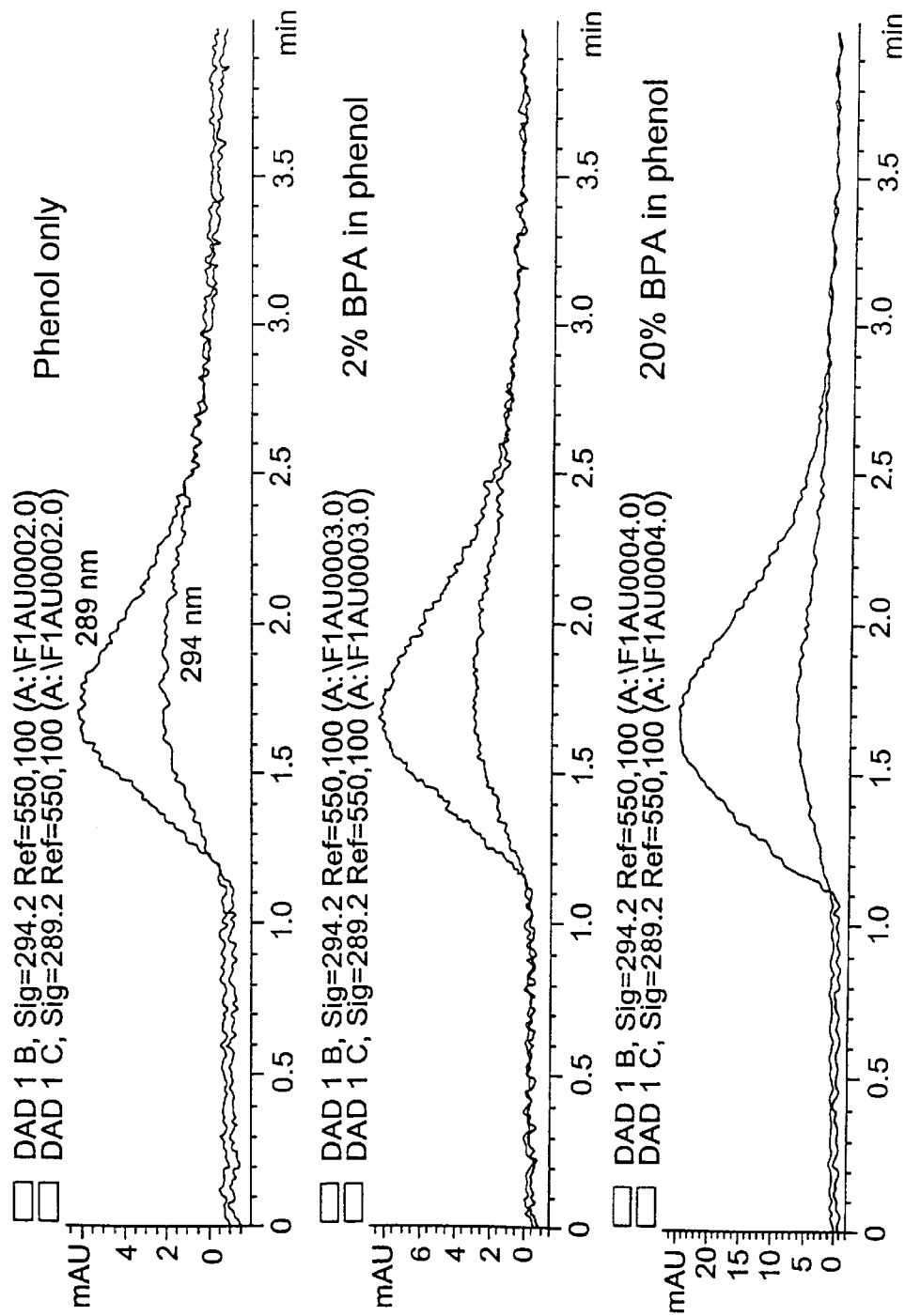
FIG. 3 shows traces corresponding to 289 nanometers (nm) and 294 nm absorbance signals for samples containing 0, 2, and 20 weight percent bisphenol A in phenol as solutions in acetonitrile.
Figure 4:
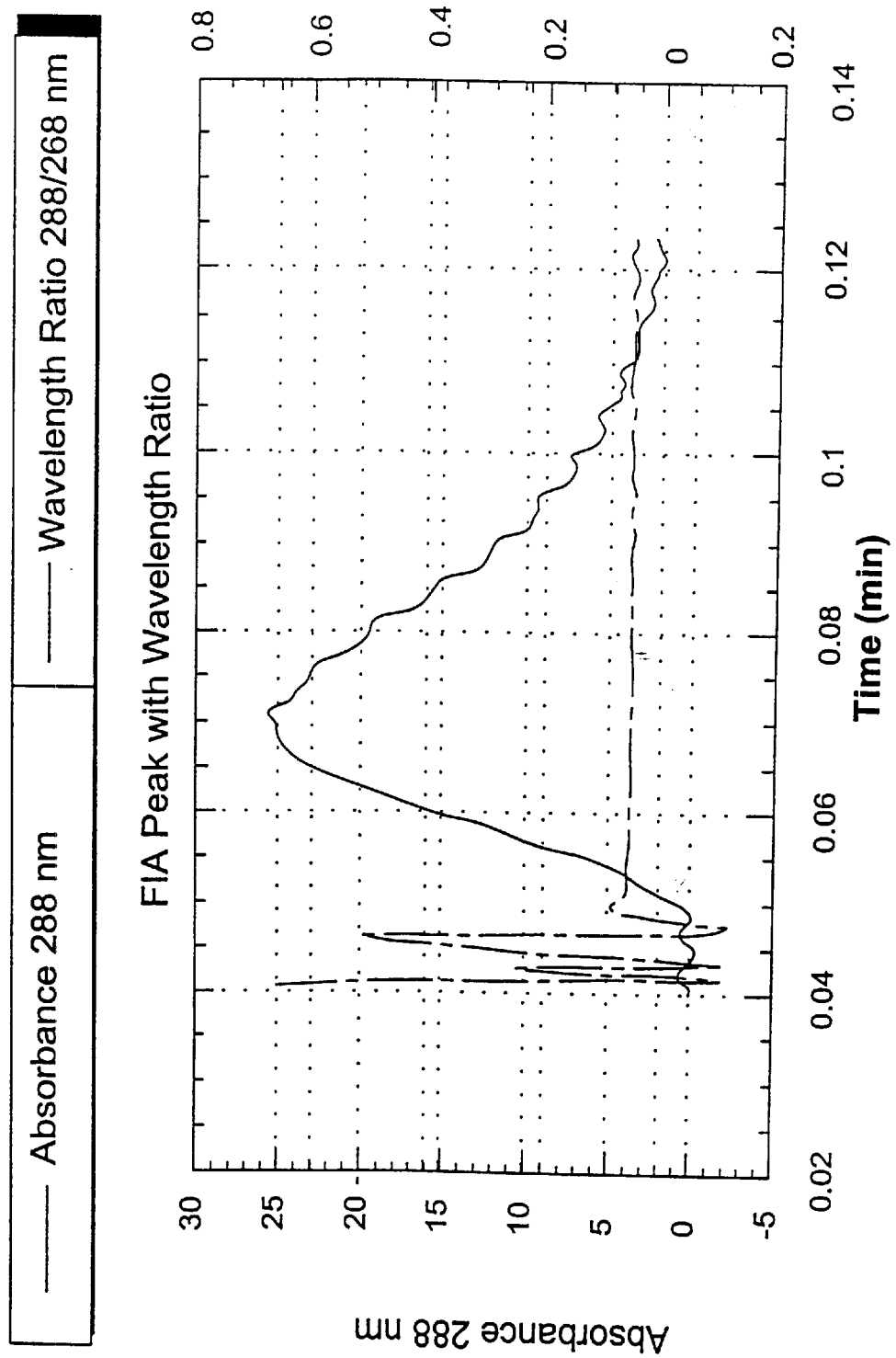
FIG. 4 is an overlay plot of the absorbance at 288 nm and the absorbance ratio ($A_{289}/A_{294}$) for a sample containing 2 weight percent BPA in phenol dissolved in acetonitrile.
Figure 5:
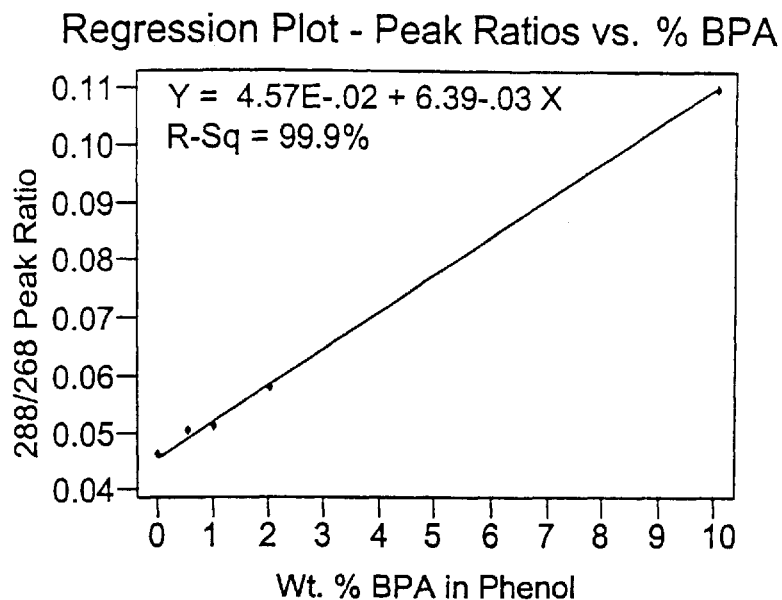
FIG. 5 is a plot of the absorbance ratio ($A_{289}/A_{294}$) for five calibration samples having bisphenol A concentrations ranging from 0 to about 10 weight percent and a phenol concentration of about 10 weight percent in acetonitrile.

Although the spectra are very similar, subtle differences exist in the 240–300 nm range. Overlay plots of the 289 and 294 nm absorbance intensities across the peak are shown for 0%, 2% and 20% BPA in phenol in FIG. 3. The ratio of absorbances at 289 and 294 nm was observed to increase with increasing BPA concentration. An overlay plot of the absorbance ratio at 289 nm and 294 nm ($A_{289}/A_{294}$) and the absorbance at 288 for 2 weight percent BPA and 10 weight percent phenol in acetonitrile is shown in FIG. 4. At the beginning and end tails of the elution peak the ratio $A_{289}/A_{294}$ becomes noisy, while it is relatively constant across the center of the peak. A calibration was constructed using BPA concentrations of 0.5, 1.0, 2.0, and 10.0 weight percent and 10 weight percent phenol dissolved in acetonitrile and plotting BPA concentration vs. the absorbance ratio ($A_{288}/A_{268}$). The resulting data are provided in Table 1 and plotted in FIG. 5 and show good linearity with an $R^2$ value of 0.999. This experiment shows that bisphenol A concentrations in the range 0.5 to 20 weight percent can be rapidly and accurately determined in the presence of phenol concentrations as much as 500 times greater.

TABLE 1

| Bisphenol A concentration (weight percent) | $A_{288}/A_{268}$ |
|---|---|
| 0 | 0.0464 |
| 0.50 | 0.0501 |
| 1.0 | 0.0509 |
| 2.0 | 0.0577 |
| 10.0 | 0.1099 |

EXAMPLE 2

The diode array data from Example 1 were used to construct a chemometric calibration model using partial least squares (PLS) techniques known in the art. The calibration model was derived using the absorbance at each of the measured wavelengths in the range from 238 to 298 nm. All of the spectra across the elution profile of the peak were used. The quantification of a sample was done using the spectra from the elution profile of a sample spanning the same wavelength range. The raw data for the method was a data matrix where the rows are the individual sample spectra and the columns are the absorbances at each of the measured wavelengths.

By using data from diodes spanning 238 to 298 nm by 2 nm, the analysis was more sensitive and more accurate than the peak ratio model.

All calculations were performed using the matrix handling methods in MATLAB 5.0 and routines from the PLS_Toolbox (Eigenvector Research Inc. Manson, Wash.) running on a personal computer with a Pentium II microprocessor.

The model used samplewise autoscaled data. Autoscaling is a data preprocessing technique where each point in the sample spectrum is subtracted from the mean of the spectrum and then divided by the standard deviation of the spectrum. This transform removes the variation in the data due to the absolute intensity differences of the spectra. The variation in the data due to the differences in composition is reflected in the altering of the shape of the spectrum. Measurement of this variation is made easier once the variation due to absolute amount is removed by auto scaling.

The data were divided into training and validation data sets. Twenty percent of the samples were used for the validation set. The validation samples were randomly chosen from each of the four levels used for this study.

Figure 6:
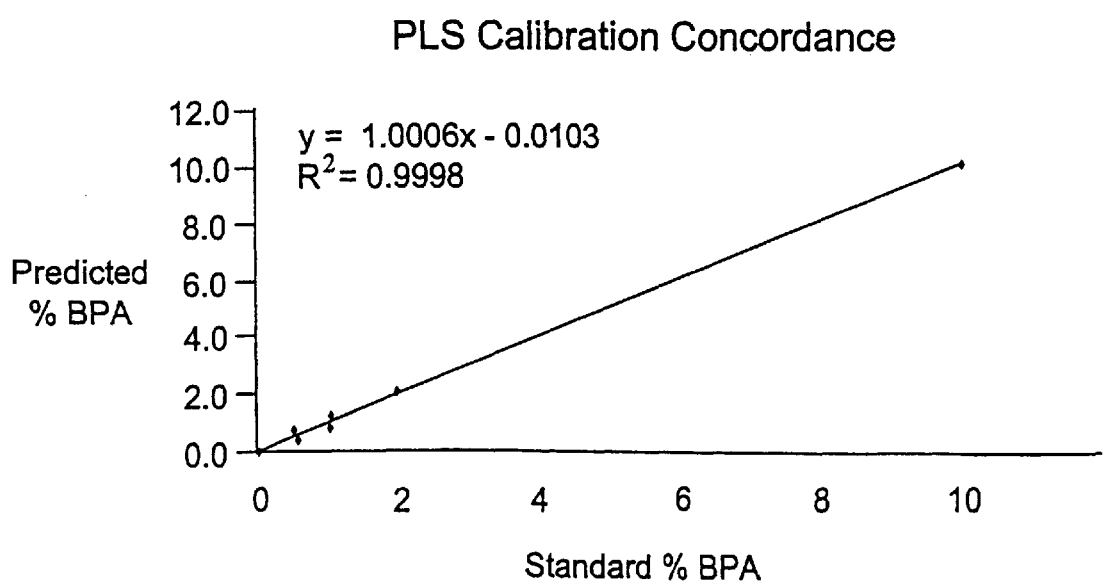
FIG. 6 is a plot of predicted versus actual bisphenol A concentration in an acetonitrile solution containing 10 weight percent phenol; each data point corresponds to one of 22 samples used in a training set for partial least squares analysis.
Figure 7:
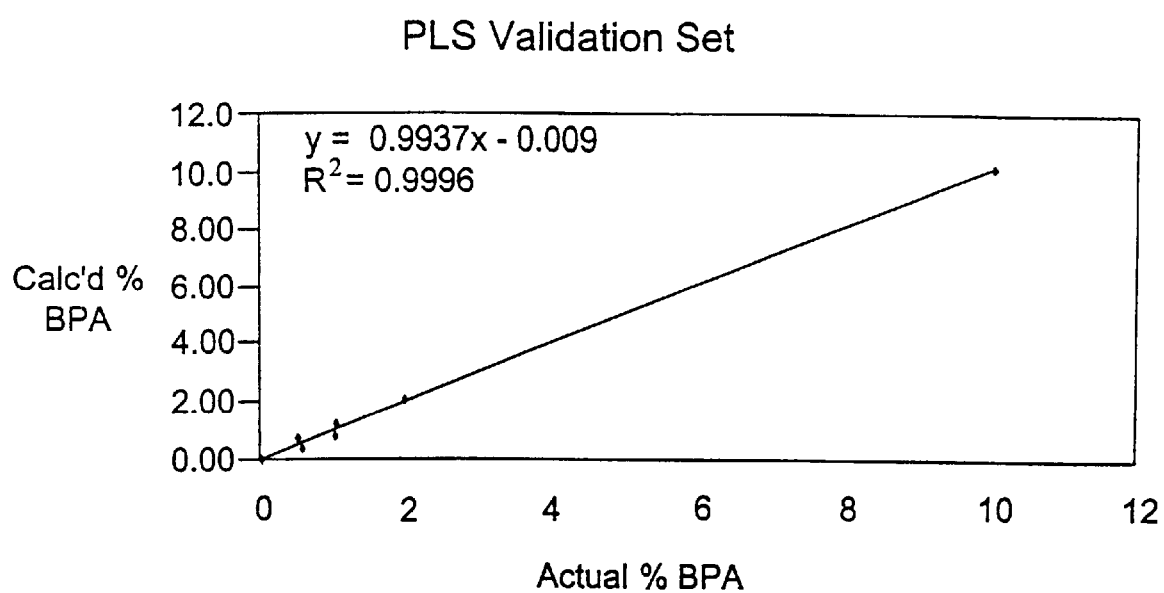
FIG. 7 is a plot of predicted versus actual bisphenol A concentration in an acetonitrile solution containing 10 weight percent phenol; each data point corresponds to one of five samples used in a validation set for partial least squares analysis.

A two component model was found to capture over 99% of the variation in the calibration data set. The resulting calibration concordance shows excellent linearity in the concentration range modeled with an $R^2$ value of 0.9998. Observed and predicted values of phenol and bisphenol A concentrations are presented in Table 2 and plotted in FIG. 6. The validation data, provided in Table 3 and FIG. 7, show excellent agreement between observed and predicted values with an $R^2$ value of 0.9996. The major source of variation in the data is due to the changes in the phenol and BPA concentrations. This variation is adequately captured using a two component model.

TABLE 2

| Bisphenol A concentration (weight percent) | | Phenol concentration (weight percent) | |
|---|---|---|---|
| actual | predicted | actual | predicted |
| 10 | 10 | 0 | 0 |
| 10 | 10 | 0 | 0 |
| 10 | 10 | 0 | 0 |
| 0 | 0.04 | 10 | 9.996 |
| 0 | −0.02 | 10 | 10.002 |
| 0 | 0.01 | 10 | 9.99 |
| 0.050 | 0.044 | 9.950 | 9.956 |
| 0.050 | 0.042 | 9.950 | 9.958 |
| 0.050 | 0.059 | 9.950 | 9.941 |
| 0.100 | 0.094 | 9.900 | 9.906 |
| 0.100 | 0.088 | 9.900 | 9.912 |
| 0.100 | 0.101 | 9.900 | 9.899 |
| 0.100 | 0.109 | 9.900 | 9.891 |
| 0.200 | 0.201 | 9.800 | 9.799 |
| 0.200 | 0.198 | 9.800 | 9.802 |
| 0.200 | 0.198 | 9.800 | 9.802 |
| 0.200 | 0.199 | 9.800 | 9.801 |
| 1.00 | 1.001 | 9.000 | 8.999 |
| 1.00 | 0.997 | 9.000 | 9.003 |
| 1.00 | 0.999 | 9.000 | 9.001 |
| 1.00 | 1.000 | 9.000 | 9.000 |
| 1.00 | 1.002 | 9.000 | 8.998 |

TABLE 3

| Bisphenol A concentration (weight percent) | | Phenol concentration (weight percent) | |
|---|---|---|---|
| actual | predicted | actual | predicted |
| 0.50 | 0.63 | 99.50 | 99.37 |
| 1.00 | 0.95 | 99.00 | 99.05 |
| 2.00 | 1.91 | 98.00 | 1.94 |
| 2.00 | 1.94 | 98.00 | 98.06 |
| 10.00 | 9.96 | 90.00 | 90.04 |

While preferred embodiments have been shown and described, various modifications and substitutions may be made thereto without departing from the spirit and scope of the invention. In particular, the method has been demonstrated for analysis of aromatic polycarbonate samples prepared by melt synthesis, but it is suitable for analysis of polycarbonates and aromatic polyesters prepared by various means. Accordingly, it is to be understood that the present invention has been described by way of illustration and not limitation.

All cited patents and other references are incorporated herein by reference.

What is claimed is:

1. An analytical flow system, comprising:

a solvent delivery system;

a sample injector for injecting into the solvent delivery system a known volume of each of a plurality of analytical samples, each analytical sample comprising a dihydric phenol and a monohydric phenol;

an absorbance detector in fluid communication with the solvent delivery system for detecting the absorbance of the known volume of each analytical sample at at least two wavelength ranges; and a computer for determining the concentration of the dihydric phenol in each analytical sample based on the absorbance of the known volume of each analytical sample at at least two wavelength ranges;

wherein the analytical system enables a total analysis time not greater than about 5 minutes per sample.

2. The analytical system of claim 1, wherein the absorbance detector comprises a diode array detector.

3. The analytical system of claim 1, further comprising a sample preparation module in flow communication with and upstream of the sample injector.

4. The analytical system of claim 1, wherein computer control of the solvent delivery system, the sample preparation module, the sample injector, and the absorbance detector enables analysis of the plurality of analytical samples without human intervention.

* * * * *